US010808228B2

(12) United States Patent
Agnew et al.

(10) Patent No.: US 10,808,228 B2
(45) Date of Patent: Oct. 20, 2020

(54) METHODS FOR INCREASING THE INFECTIVITY OF VIRUSES UTILIZING ALKYNE-MODIFIED FATTY ACIDS

(71) Applicants: Life Technologies Corporation, Carlsbad, CA (US); The Johns Hopkins University, Baltimore, MD (US)

(72) Inventors: Brian Agnew, Carlsbad, CA (US); David Graham, Baltimore, MD (US)

(73) Assignees: THE JOHNS HOPKINS UNIVERSITY, Baltimore, MD (US); LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 15/865,713

(22) Filed: Jan. 9, 2018

(65) Prior Publication Data

US 2018/0171306 A1 Jun. 21, 2018

Related U.S. Application Data

(62) Division of application No. 14/374,404, filed as application No. PCT/US2013/023047 on Jan. 25, 2013, now Pat. No. 9,890,361.

(60) Provisional application No. 61/591,047, filed on Jan. 26, 2012.

(51) Int. Cl.

*C12N 7/00* (2006.01)
*A61K 39/00* (2006.01)
*A61K 48/00* (2006.01)

(52) U.S. Cl.

CPC ................ *C12N 7/00* (2013.01); *A61K 39/00* (2013.01); *A61K 48/00* (2013.01); *C12N 2740/16034* (2013.01); *C12N 2740/16045* (2013.01); *C12N 2740/16051* (2013.01); *C12N 2810/10* (2013.01)

(58) Field of Classification Search

CPC ............ C12N 7/00; C12N 2740/16045; C12N 2740/16051

See application file for complete search history.

(56) References Cited

U.S. PATENT DOCUMENTS

| | | | |
|---|---|---|---|
| 7,169,411 | B1 | 1/2007 | Kabanov et al. |
| 2005/0214751 | A1 | 9/2005 | Reiss et al. |
| 2009/0181402 | A1 | 7/2009 | Finn et al. |
| 2010/0203647 | A1 | 8/2010 | Hang et al. |
| 2011/0263001 | A1 | 10/2011 | Lakshmipathy et al. |

FOREIGN PATENT DOCUMENTS

| | | | |
|---|---|---|---|
| EP | 0659885 | A1 | 6/1995 |
| EP | 1335019 | A1 | 8/2003 |
| WO | 01/20989 | A1 | 3/2001 |
| WO | 2007/085630 | A1 | 8/2007 |
| WO | 2011/133929 | A2 | 10/2011 |
| WO | 2012/016044 | A1 | 2/2012 |
| WO | 2013/112778 | A1 | 8/2013 |

OTHER PUBLICATIONS

Rustan, A. C., and C. A. Devron, 2005, Fatty acids: structures and properties, Encyclopedia of Life Sciences, John Wiley & Sons, Ltd., pp. 1-7.*

Ghazarian, H., et al., 2011, A glycobiology review: carbohydrates, lectins and implications in cancer therapeutics, Acta Histochemica 113:236-247.*

Holstein, S. A., and R. J. Hohl, 2004, Isoprenoids: remarkable diversity of form and function, Lipids 39(4):293-309.*

Villamor, E., et al., 2007, Long-chain n-6 polyunsaturated fatty acids in breast milk decrease the risk of HIV transmission through breast feeding, Am. J. Clin. Nutr. 86:682-689.*

Lee, D. Y. W., et al., 2009, Palmitic acid is a novel CD4 fusion inhibitor that blocks HIV entry and infection, AIDS Res. Human Retrovir. 25(12):1231-1243.*

Go, E. P., et al., 2008a, Glycosylation site-specific analysis of HIV envelope proteins (JR-FL and CON-S) reveals major differences in glycsoylation site occupancy, glycoform profiles, and antigenic epitopes' accessibility, J. Proteome Res. 7:1669-1674.*

Go, E. P., et al., 2008a, Glycosylation site-specific analysis of HIV envelope proteins (JR-FL and CON-S) reveals major differences in glycsoylation site occupancy, glycoform profiles, and antigenic epitopes' accessibility, J. Proteome Res. 7:1669-1674 (supplemental data).*

Shen, R., et al., 2014, HIV-1 envelope glycan moieties modulate HIV-1 transmission, J. Virol. 88(24):14258-14267.*

Lorizate, M., and H.-G. Krausslich, 2011, Role of lipids in virus replication, Cold Spring Harbor Perspect. Biol. 3:1-21.*

International Search Report dated Apr. 1, 2013 from International Application No. PCT/US2013/023047, pp. 1-4.

Zeng et al., "Chemoselective Modification of Turnip Yellow Mosaic Virus by Cu(I) Catalyzed Azide-Alkyne 1, 3-Dipolar-Cycloaddition Reaction and Its Application in Cell Binding", Bioconjugate Chemistry, vol. 22, No. 1, Jan. 19, 2011, pp. 58-66.

Extended European Search Report dated Sep. 14, 2015 from European Patent Application No. 13740994.2, pp. 1-6.

(Continued)

*Primary Examiner* — Jeffrey S Parkin

(74) *Attorney, Agent, or Firm* — MH2 Technology Law Group, LLP

(57) ABSTRACT

Methods of using viruses labeled with alkyne-modified biomolecules, such as fatty acids, carbohydrates and lipids, to treat a plant, an insect or an animal infected with a virus or to increase the infectivity of a virus, such as the human immunodeficiency virus, are provided. Also provided are methods of labeling a virus, such as human immunodeficiency virus, with an alkyne-modified biomolecule, such as a fatty acid, a carbohydrate, or an isoprenoid lipid. The viruses labeled with alkyne-modified biomolecules may be combined with a pharmaceutically acceptable excipient to produce a pharmaceutical composition, optionally containing another anti-viral agent and/or a delivery agent, such as a liposome.

14 Claims, No Drawings

(56) References Cited

OTHER PUBLICATIONS

Singapore Search Report dated Jul. 29, 2015 from Singapore Patent Application No. 11201404361U, pp. 1-9.
Rustan et al., “Fatty Acids: Structures and Properties”, Encyclopedia of Life Sciences, 2005, John Wiley & Sons, Ltd, pp. 1-7.
Ghazarian et al., “A glycobiology review: Carbohydrates, lectins and implications in cancer therapeutics”, Acta Histochemica, 2011, vol. 113, pp. 236-247.
Holstein et al., “Isoprenoids: Remarkable Diversity of Form and Function”, Lipds, 2004, vol. 39, No. 4, pp. 293-309.
Villamor et al., Long-chain n-6 poyunsaturated fatty acids in breast milk decrease the risk of HIV transmission through breastfeeding, Am J. Clin Nutri., 2007, vol. 86, pp. 682-689.
Lee et al., “Palmitic Acid is a Novel CD4 Fusion Inhibitor That Blocks HIV Entry and Infection”, Aids Research and Human Retroviruses, 2009, vol. 25, No. 12, pp. 1231-1243.
Go et al., “Glycosylation Site-Specific Analysis of HIV Envelope Proteins (JR-FL and CON-S) Reveals Major Differences in Glycosylation Site Occupancy, Glycoform Profiles, and Antigenic Epitopes’ Accessibility”, Journal of Proteome Research, 2008, vol. 7, pp. 1669-1674 and Supplemental Data.
Shen et al., “HIV-1 Envelope Glycan Moieties Modulate HIV-1 Transmission”, Journal of Virology, Dec. 2014, vol. 88, No. 24, pp. 14258-14267.
Lorizate et al., “Role of Lipids in Virus Replication”, Cold Spring Harbor Perspectives in Biology, 2011, vol. 3, pp. 1-21.

* cited by examiner

METHODS FOR INCREASING THE INFECTIVITY OF VIRUSES UTILIZING ALKYNE-MODIFIED FATTY ACIDS

CROSS REFERENCE

This application is a divisional application of U.S. patent application Ser. No. 14/374,404 (allowed), filed 24 Jul. 2014, which is a U.S. National Stage application of PCT/US2103/023047 filed Jan. 25, 2013, which claims priority to U.S. Provisional Application Ser. No. 61/591,047, filed Jan. 26, 2012, which are hereby incorporated by reference in their entirety.

BACKGROUND

Viruses infecting humans, animals, plant and insects are well known. Infection of these hosts by viruses can result in disease unless an appropriate immunological response is available to neutralize the infection. Vaccines capable of eliciting the immunological components necessary for an immunological response have been developed to prevent infection by viruses in humans and animals, with notable examples being the flu vaccine and the rabies vaccine, respectively.

Vaccines typically contain an agent that resembles a disease-causing virus. The agent can be a weakened (attenuated) or killed (inactivated) form of the virus. The production of a whole virus vaccine generally begins with the virus being grown either in primary cells (e.g., flu virus) or in continuous cell lines such as cultured human or animal cells (e.g., polio virus). In order to propagate the virus in such cells, the virus must first infect the cells. Accordingly, there is a need for methods of increasing the infectivity of viruses for the making of vaccines.

Viruses also have use in the preparation of viral vectors used by researchers to deliver genetic material into cells and organisms in both a research or gene therapy setting. Such viral vectors are non-naturally occurring viruses. In order to deliver genetic material to a cell, the vectors need to infect a cell. Accordingly, there is a need for viral vectors having increased infectivity to improve the amount of genetic material that can be delivered to target cells or organisms.

SUMMARY

One aspect of the present invention is a method of enhancing the infectivity of a human immunodeficiency virus, the method comprising contacting the virus with an alkyne-modified fatty acid, an alkyne-modified carbohydrate, an alkyne-modified isoprenoid lipid, or physiologically acceptable salt thereof in an amount effective to enhance the infectivity of the virus.

In some embodiments, the virus is in a cell. In some of these, the cell is a human animal cell or a non-human animal cell.

In some embodiments, the human immunodeficiency virus is HIV-1.

In some embodiments, the alkyne-modified fatty acid or physiologically acceptable salt thereof has the formula:

$$Y—CH_2—X—CO_2H \quad [I]$$

wherein, Y is H or an ethynyl group; and when Y is an ethynyl group, X is a linear or branched carbon chain comprising 6 to 28 carbons, wherein one or more of said carbons may be independently replaced by an oxygen, selenium, silicon, sulfur, SO, $SO_2$ or $NR_1$, or wherein one or more pairs of said carbons adjacent to one another may be attached to one another by a double or triple bond; or when Y is H, X is a linear or branched carbon chain comprising 6 to 28 carbons, wherein at least one hydrogen on one of said carbons is replaced with an ethynyl group and wherein one or more of said carbons not having an the ethynyl group attached thereto may be independently replaced by an oxygen, selenium, silicon, sulfur, SO, $SO_2$ or $NR_1$, or wherein one or more pairs of said carbons adjacent to one another and not having an ethynyl group attached thereto may be attached to one another by a double or triple bond; wherein, $R_1$ is H or an alkyl comprising 1 to 6 carbons.

In certain embodiments comprising contacting the virus with [I], Y is an ethynyl group.

In certain embodiments comprising contacting the virus with [I], X is a linear carbon chain.

In certain embodiments comprising contacting the virus with [I 1], X is a carbon chain comprising 8 to 15 carbons.

In certain embodiments comprising contacting the virus with [I], X is a carbon chain in which all of the carbons of the carbon chain are carbon.

In certain embodiments comprising contacting the virus with [I], X is a carbon chain in which all of the bonds between the carbons of the carbon chain are single bonds.

In certain embodiments comprising contacting the virus with [I], the alkyne-modified fatty acid is 15-ethynylpentadecanoic acid or physiologically acceptable salt thereof.

In certain embodiments comprising contacting the virus with [I], the alkyne-modified fatty acid is 12-ethynyldodecanoic acid or physiologically acceptable salt thereof.

In certain embodiments comprising contacting the virus with [I], the alkyne-modified fatty acid is

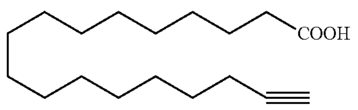

[II]

or physiologically acceptable salt thereof.

In certain embodiments comprising contacting the virus with [I], the alkyne-modified fatty acid is

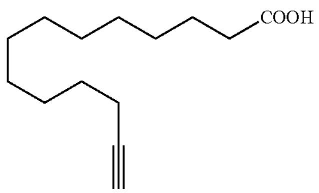

[III]

or physiologically acceptable salt thereof.

In certain embodiments comprising contacting the virus with [I], Y is an ethynyl group, X is a linear carbon chain, and the linear carbon chain comprises 8 to 15 carbons. In some of these, all of the carbons of the carbon chain are carbon, while in others, all of the bonds between the carbons of the carbon chain are single bonds.

In some embodiments, the contacting is performed in a solution comprising at least one of animal serum, amino acids, buffers, fatty acids, glucose, hormones, inorganic salts, lipids, metal ion chelators, peptides, surfactants, trace metals, and vitamins.

Another aspect of the present invention is a method of enhancing the infectivity of a human immunodeficiency virus, the method comprising contacting a cell infected with the virus with an alkyne-modified fatty acid, an alkyne-modified carbohydrate, an alkyne-modified isoprenoid lipid, or physiologically acceptable salt thereof in an amount effective to enhance the infectivity of the virus.

In some embodiments, the cell is a human animal cell or a non-human animal cell.

In some embodiments, the human immunodeficiency virus is HIV-1.

In some embodiments, the alkyne-modified fatty acid or physiologically acceptable salt thereof has the formula [I], the substituents of which are described above.

In certain embodiments comprising contacting a cell infected with the virus with [I], Y is an ethynyl group.

In certain embodiments comprising contacting a cell infected with the virus with [I], X is a linear carbon chain.

In certain embodiments comprising contacting a cell infected with the virus with [I], X is a carbon chain comprising 8 to 15 carbons.

In certain embodiments comprising contacting a cell infected with the virus with [I], X is a carbon chain in which all of the carbons of the carbon chain are carbon.

In certain embodiments comprising contacting a cell infected with the virus with [1], X is a carbon chain in which the all of the bonds between the carbons of the carbon chain are single bonds.

In certain embodiments comprising contacting a cell infected with the virus with [I], the alkyne-modified fatty acid is 15-ethynylpentadecanoic acid or physiologically acceptable salt thereof.

In certain embodiments comprising contacting a cell infected with the virus with [I], the alkyne-modified fatty acid is 12-ethynyldodecanoic acid, or physiologically acceptable salt thereof.

In certain embodiments comprising contacting a cell infected with the virus with [I], the alkyne-modified fatty acid is [II] or physiologically acceptable thereof.

In certain embodiments comprising contacting a cell infected with the virus with [I], the alkyne-modified fatty acid is [III] or physiologically acceptable thereof.

In certain embodiments comprising contacting a cell infected with the virus with [I], Y is an ethynyl group, X is a linear carbon chain, and the linear carbon chain comprises 8 to 15 carbons. In some of these, all of the carbons of the carbon chain are carbon, while in others, all of the bonds between the carbons of the carbon chain are single bonds.

In some embodiments, the contacting is performed in a solution comprising at least one of animal serum, amino acids, buffers, fatty acids, glucose, hormones, inorganic salts, lipids, metal ion chelators, peptides, surfactants, trace metals, and vitamins.

Another aspect of the present invention is a human immunodeficiency virus comprising an alkyne-modified fatty acid moiety, an alkyne-modified carbohydrate moiety, or an alkyne-modified isoprenoid lipid moiety; wherein the moiety is non-naturally occurring.

In some embodiments, the virus is HIV-1.

In some embodiments, the virus is inactivated.

In some embodiments, the virus is attenuated.

In some embodiments, the alkyne-modified fatty acid moiety has the formula:

$$Y—CH_2—X—CO— \quad [IV]$$

wherein, Y is H or an ethynyl group; and when Y is an ethynyl group, X is a linear or branched carbon chain comprising 6 to 28 carbons, wherein one or more of said carbons may be independently replaced by an oxygen, selenium, silicon, sulfur, SO, $SO_2$ or $NR_1$, or wherein one or more pairs of said carbons adjacent to one another may be attached to one another by a double or triple bond; or when Y is H, X is a linear or branched carbon chain comprising 6 to 28 carbons, wherein at least one hydrogen on one of said carbons is replaced with an ethynyl group and wherein one or more of said carbons not having an the ethynyl group attached thereto may be independently replaced by an oxygen, selenium, silicon, sulfur, SO, $SO_2$ or $NR_1$, or wherein one or more pairs of said carbons adjacent to one another and not having an ethynyl group attached thereto may be attached to one another by a double or triple bond; wherein, $R_1$ is H or an alkyl comprising 1 to 6 carbons.

In certain embodiments comprising [IV], Y is an ethynyl group.

In certain embodiments comprising [IV], X is a linear carbon chain.

In certain embodiments comprising [IV], X is a carbon chain comprising 8 to 15 carbons.

In certain embodiments comprising [IV], X is a carbon chain in which all of the carbons of the carbon chain are carbon.

In certain embodiments comprising [IV], X is a carbon chain in which all of the bonds between the carbons of the carbon chain are single bonds.

In certain embodiments comprising [IV], the alkyne-modified fatty acid moiety is 15-ethynylpentadecanyl.

In certain embodiments comprising [IV], the alkyne-modified fatty acid moiety is 12-ethynyldodecanyl.

In certain embodiments comprising [IV], the alkyne-modified fatty acid moiety is

[V]

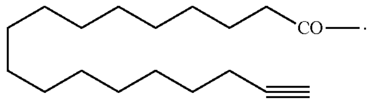

In certain embodiments comprising [IV], the alkyne-modified fatty acid moiety is

[VI]

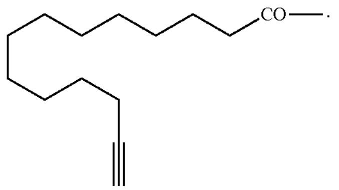

In certain embodiments comprising [IV], Y is an ethynyl group, X is a linear carbon chain, and the linear carbon chain comprises 8 to 15 carbons. In some of these, all of the carbons of the carbon chain are carbon, while in others, all of the bonds between the carbons of the carbon chain are single bonds.

In certain embodiments comprising [IV], the alkyne-modified fatty acid moiety is attached to the virus by an amide or a thioester bond.

Another aspect of the present invention is a composition comprising a human immunodeficiency virus comprising an alkyne-modified fatty acid moiety, an alkyne-modified carbohydrate moiety, or an alkyne-modified isoprenoid lipid moiety; wherein the moiety is non-naturally occurring.

In some embodiments, the virus is HIV-1.

In some embodiments, the virus is inactivated.

In some embodiments, the virus is attenuated.

In some embodiments, the alkyne-modified fatty acid moiety has the formula [IV], the substituents of which are described above.

In certain embodiments comprising [IV], Y is an ethynyl group.

In certain embodiments comprising [IV], X is a linear carbon chain.

In certain embodiments comprising [IV], X is a carbon chain comprising 8 to 15 carbons.

In certain embodiments comprising [IV], X is a carbon chain in which all of the carbons of the carbon chain are carbon.

In certain embodiments comprising [IV], X is a carbon chain in which all of the bonds between the carbons of the carbon chain are single bonds.

In certain embodiments comprising [IV], the alkyne-modified fatty acid moiety is 15-ethynylpentadecanyl.

In certain embodiments comprising [IV], the alkyne-modified fatty acid moiety is 12-ethynyldodecanyl.

In certain embodiments comprising [IV], the alkyne-modified fatty acid moiety is [V].

In certain embodiments comprising [IV], the alkyne-modified fatty acid moiety is [VI].

In certain embodiments comprising [IV], Y is an ethynyl group, X is a linear carbon chain, and the linear carbon chain comprises 8 to 15 carbons. In some of these, all of the carbons of the carbon chain are carbon, while in others, all of the bonds between the carbons of the carbon chain are single bonds.

In certain embodiments comprising [IV], the alkyne-modified fatty acid moiety is attached to the virus by an amide or a thioester bond.

In some embodiments, the composition further comprises a pharmaceutically acceptable excipient.

Definitions

Unless defined otherwise, all technical and scientific terms used herein have the same meaning as commonly understood by one of ordinary skill in the art to which this invention is related. In order that the present invention may be more readily understood, certain terms are first defined. Additional definitions are set forth throughout the detailed description. In case of conflict, the present specification, including definitions, will control.

As used herein, "alkyne-modified fatty acid" refers to a fatty acid that comprises an alkyne group and has the following formula, R-alkyne where R comprises a hydrocarbon chain with at least one carboxylic acid functional group, which is usually, although not necessarily, at a terminal position.

As used herein, "alkyne-modified carbohydrate" refers to a carbohydrate that comprises an alkyne group and has the following formula, R-alkyne where R is a carbohydrate.

As used herein, "alkyne-modified isoprenoid lipid" refers to an isoprene-containing lipid, or derivative thereof. The alkyne-modified isoprenoid comprises an alkyne group and has the following formula, R-alkyne where R is an isoprene-containing lipid, such as the $C_{15}$ farnesyl isoprenoid lipid or the $C_{20}$ geranylgeranyl isoprenoid lipid, or a derivative thereof, including, but not limited to, an ethynyl farnesyl diphosphate, an ethynyl farnesyl alcohol, an ethynyl geranylgeranyl diphosphate, or an ethynyl geranylgeranyl alcohol.

As used herein, "animal virus" refers to a virus that infects a non-human animal or human animal cell. A non-human animal virus infects non-human animal cells. In certain instances, a virus that infects non-human animal cells is also capable of infecting human animal cells. A human animal virus infects human animal cells. In certain instances, a virus that infects human animal cells is also capable of infecting non-human animal cells.

As used herein, "biomolecule," refers to proteins, peptides, amino acids, glycoproteins, nucleic acids, nucleotides, nucleosides, oligonucleotides, sugars, oligosaccharides, lipids, hormones, proteoglycans, carbohydrates, polypeptides, polynucleotides, polysaccharides, which having characteristics typical of molecules found in living organisms and may be naturally occurring or may be artificial (not found in nature and not identical to a molecule found in nature).

As used herein, "click chemistry," refers to the copper(I)-catalyzed variant of the Huisgen cycloaddition or the 1,3-dipolar cycloaddition between an azide and a terminal alkyne to form a 1,2,4-triazole. Such chemical reactions can use, but are not limited to, simple heteroatomic organic reactants and are reliable, selective, stereospecific, and exothermic.

As used herein, "cycloaddition" refers to a chemical reaction in which two or more π (pi)-electron systems (e.g., unsaturated molecules or unsaturated parts of the same molecule) combine to form a cyclic product in which there is a net reduction of the bond multiplicity. In a cycloaddition, the π (pi) electrons are used to form new π (pi) bonds. The product of a cycloaddition is called an "adduct" or "cycloadduct". Different types of cycloadditions are known in the art including, but not limited to, [3+2] cycloadditions and Diels-Alder reactions. [3+2] cycloadditions, which are also called 1,3-dipolar cycloadditions, occur between a 1,3-dipole and a dipolarophile and are typically used for the construction of five-membered heterocyclic rings. The term "[3+2] cycloaddition" also encompasses "copperless" [3+2] cycloadditions between azides and cyclooctynes and difluorocyclooctynes described by Bertozzi et al. J. Am. Chem. Soc., 2004, 126:15046-15047.

As used herein, "DNA virus" refers to a virus that has deoxyribonucleic acid (DNA) as its genetic material. DNA viruses are usually double stranded but may also be single stranded.

As used herein, "gene therapy" refers to the transfer of heterologous nucleic acid, such as DNA or RNA, into target cells of a human animal, non-human animal, plant or insect having a disorder or condition for which such therapy or treatment is sought. As used herein, gene therapy includes, but is not limited to, the transfer of heterologous nucleic acid, such as DNA, into a virus, which can be transferred to a human animal, non-human animal, plant or insect, with a disorder or condition for which such therapy or treatment is sought. The nucleic acid, such as DNA, is introduced into the selected target cells, such as directly or indirectly, in a manner such that the heterologous nucleic acid, such as DNA, is expressed and a therapeutic product encoded thereby is produced. Alternatively, the heterologous nucleic acid, such as DNA, can in some manner mediate expression of DNA that encodes the therapeutic product, or it can encode a product, such as a peptide or RNA that is in some manner a therapeutic product, or which mediates, directly or indirectly, expression of a therapeutic product. Gene therapy also includes, but is not limited to, the delivery of nucleic acid encoding a gene product that replaces a defective gene or supplements a gene product produced by the human animal, non-human animal, plant, insect, or the cell thereof in which it is introduced. The introduced nucleic acid can include, but is not limited to, a nucleic acid encoding a therapeutic compound. The heterologous nucleic acid, such as DNA, encoding the therapeutic product can be modified prior to introduction into the cells of the afflicted host in order to enhance or otherwise alter the product or expression thereof. Gene therapy can also include, but is not limited to, the delivery of an inhibitor or repressor or other modulator of gene expression.

As used herein, "glycoprotein" refers to a protein that has been glycosylated and those that have been enzymatically modified, in vivo or in vitro, to comprise a carbohydrate group.

As used herein, "HIV" and "human immunodeficiency virus" refer to human immunodeficiency virus 1 and 2 (HIV-1 and HIV-2).

As used herein, "infectivity" refers to the ability of a virus to enter or exit a cell.

As used herein, "insect virus" refers to a virus that infects insect cells. Certain insect viruses, such as, for example, unmodified baculovirus or modified baculovirus (BacMam), can also infect non-human animal and/or human animal cells.

As used herein, "plant virus" refers to a virus that infects plant cells.

As used herein, "pharmaceutically acceptable excipient" includes solvents, dispersion media, diluents, coatings, anti-bacterial and antifungal agents, isotonic and absorption delaying agents, etc., that are compatible with pharmaceutical administration. Use of these agents for pharmaceutically active substances is well known in the art.

As used herein, "physiologically acceptable salt" refers to inorganic or organic salts, including, but not limited to, buffer salts which are not deleterious to cell health or integrity. Use of these salts for physiologically acceptable salts is well known in the art.

As used herein, "protein" and "polypeptide" are used in a generic sense to include polymers of amino acid residues of any length. The term "peptide" is used herein to refer to polypeptides having less than 100 amino acid residues, typically less than 10 amino acid residues. The terms apply to amino acid polymers in which one or more amino acid residues are an artificial chemical analogue of a corresponding naturally occurring amino acid, as well as to naturally occurring amino acid polymers.

As used herein, "reporter molecule" refers to any moiety capable of being attached to a modified post translationally modified protein of the present invention, and detected either directly or indirectly. Reporter molecules include, without limitation, a chromophore, a fluorophore, a fluorescent protein, a phosphorescent dye, a tandem dye, a particle, a hapten, an enzyme and a radioisotope. Preferred reporter molecules include fluorophores, fluorescent proteins, haptens, and enzymes.

As used herein, "RNA virus" refers to a virus that has ribonucleic acid (RNA) as its genetic material. RNA viruses are usually single stranded but may also be double stranded.

As used herein, the term "subject" is intended to include human and non-human animals, plants, and insects. Subjects may include a human patient having a viral infection or other disorder, including, but not limited to, an HIV infection. The term "non-human animals" includes all vertebrates, such as non-human primates, sheep, dogs, cats, cows, goats, horses, chickens, pigs, amphibians, reptiles, etc.

As used herein, "treatment" or "treating" refers to a therapeutic or preventative measure. The treatment may be administered to a subject having a disorder which may include, but is not limited to, a medical disorder in the case where the subject is an animal, or who ultimately may acquire the disorder, in order to prevent, cure, delay, reduce the severity of, and/or ameliorate one or more symptoms of a disorder or recurring disorder, or in order to prolong the survival of a subject beyond that expected in the absence of such treatment.

As used herein, a "therapeutically effective amount" or "effective amount" means the amount of a compound that, when administered to a non-human animal or human animal, a plant, an insect, or other subject for treating a disease, is sufficient to effect such treatment for the disease. The "effective amount" will vary depending on the compound, the disease and its severity and the age, weight, etc., of the subject to be treated.

As used herein, the term "viral vector" is used according to its art-recognized meaning. It refers to a nucleic acid vector construct that includes at least one element of viral origin and can be packaged into a viral vector particle. The viral vector particles can be used for the purpose of transferring DNA, RNA or other nucleic acids into cells either in vitro or in vivo.

As used herein, "virus" refers to any of a large group of entities referred to as viruses. Viruses typically contain a protein coat surrounding an RNA or DNA core of genetic material, but no semipermeable membrane, and are capable of growth and multiplication only in living cells. Viruses for use in the methods and compositions provided herein include, but are not limited, any human animal virus, non-human animal virus, plant or insect virus. The term, "virus", includes within its scope a virus which occurs in nature, herein referred to as a "naturally occurring virus". The term, "virus", also includes within its scope naturally occurring viruses which have been genetically engineered, herein referred to as "non-naturally occurring virus". Such engineering of a viral gene or nucleic acids surrounding the gene, includes, but is not limited, to those which can alter the viral processes, such as, for example, viral infectivity, viral DNA replication, viral protein synthesis, virus particle assembly and maturation, and viral particle release. Such engineering can also introduce a site for insertion into the virus of heterologous DNA or RNA, which may include a non-viral gene, herein referred to as a "exogenous gene".

It must be noted that, as used in this specification and the appended claims, the singular form "a", "an" and "the" include plural referents unless the context dictates otherwise. Thus, for example, reference to "a virus" includes a plurality of viruses unless the context dictates otherwise.

While this invention has been particularly shown and described with references to preferred embodiments thereof, it will be understood by those skilled in the art that various changes in form and details may be made therein without departing from the scope of the invention encompassed by the appended claims. In addition, the materials, methods, and examples are illustrative only and not intended to be limiting. All publications, patent applications, patents, and other references mentioned herein are incorporated by reference in their entirety.

DETAILED DESCRIPTION

The present disclosure concerns the use of alkyne-modified biomolecules, such as fatty acids or carbohydrates, for making vaccines for treating viral infections, and for making viral vectors for in vivo gene therapy and in vitro transfection of cells as well as pharmaceutical compositions comprising a virus comprising an alkyne-modified biomolecule. Applicants have unexpectedly discovered that these alkyne-modified biomolecules have the ability to increase the infectivity of a virus when contacted therewith. It was surprisingly discovered that virus labeled with these alkyne-modified biomolecules profoundly affect viral infectivity and that labeling viruses with these alkyne-modified biomolecules increased viral entry into host cells. Without intending to be bound by any theory, it appears that post-translational modification of viral proteins with an alkyne-modified biomolecule at sites normally occupied by unmodified biomolecules, such as saturated fatty acids (e.g., myristic acid and palmitic acid), results in the increase of infectivity of the virus.

Click Chemistry

Azides and terminal or internal alkynes can undergo a 1,3-dipolar cycloaddition (Huisgen cycloaddition) reaction to give a 1,2,3-triazole. However, this reaction requires long reaction times and elevated temperatures. Alternatively, azides and terminal alkynes can undergo Copper(I)-catalyzed Azide-Alkyne Cycloaddition (CuAAC) at room temperature. Such copper(I)-catalyzed azide-alkyne cycloadditions, also known as click chemistry, is a variant of the Huisgen 1,3-dipolar cycloaddition wherein organic azides and terminal alkynes react to give 1,4-regioisomers of 1,2,3-triazoles. Examples of click chemistry reactions are described by Sharpless et al. (U.S. Patent Application Publication No. 20050222427, PCT/US03/17311; Lewis W G, et al., Angewandte Chemie-Int'l Ed. 41 (6): 1053; method reviewed in Kolb, H. C., et al., Angew. Chem. Inst. Ed. 2001, 40:2004-2021), which developed reagents that react with each other in high yield and with few side reactions in a heteroatom linkage (as opposed to carbon-carbon bonds) in order to create libraries of chemical compounds.

Click chemistry has been used to label and detect proteins of interest. For example, the CLICK-IT® (Invitrogen, Carlsbad, Calif.) reaction is a two-step labeling technique involving the incorporation of a modified metabolic precursor, such as an azide-modified fatty acid, an azide-modified carbohydrate, or an azide-modified isoprenoid lipid, into proteins as a chemical "handle" followed by the chemoselective ligation (or "click" reaction) between an azide and an alkyne. In the click reaction, the modified protein is detected with a corresponding azide- or alkyne-containing dye or hapten. The CLICK-IT® metabolic labeling reagents have been used to monitor post translational modifications of proteins, such as acylation, glycosylation, and prenylation, and include 1) azide-modified fatty acids, such as CLICK-IT® palmitic acid azide (i.e., 15-azidopentadecanoic acid) and CLICK-IT® myristic acid azide (i.e., 12-azidododecanoic acid), for labeling palmitoylated and myristoylated proteins, respectively; 2) azide-modified carbohydrates, including CLICK-IT® GalNAz (tetraacetylated N-azidoacetylgalactosamine) for labeling O-linked glycoproteins, CLICK-IT® ManNAz (tetraacetylated N-azidoacetyl-D-mannosamine) for labeling sialic acid modified glycoproteins, and CLICK-IT® GlcNAz (tetraacetylated N-azidoacetylglucosamine) for labeling O-GlcNAz-modified glycoproteins; and 3) azide-modified isoprenoid lipids, such as CLICK-IT® farnesyl alcohol azide and CLICK-IT® geranylgeranyl alcohol azide. As noted above, Applicants, have unexpectedly found that these alkyne-modified biomolecules increase the infectivity of viruses.

Glycosylation

Glycosylation is an enzymatic process in which carbohydrates are attached to proteins, lipids, or other organic molecules in a cell. Glycoproteins are biomolecules composed of proteins covalently linked to carbohydrates. Certain post-translational modifications append a sugar moiety (carbohydrate) onto a protein, thereby forming a glycoprotein. The common monosaccharides found in glycoproteins include, but are not limited to, glucose, galactose, mannose, fucose, xylose, N-acetylgalactosamine (GalNAc), N-acetylglucosamine (GlcNAc) and N-acetylneuraminic acid (NANA, also known as sialic acid). N-acetyl-D-mannosamine (ManNAc) is a precursor of the neuraminic acids, including NANA. Two of the same or different monosaccharides can join together to form a disaccharide. The addition of more monosaccharides results in the formation of oligosaccharides of increasing length. In addition, the sugar moiety can be a glycosyl group.

In glycoproteins, the carbohydrates can be linked to the protein component by either N-glycosylation or O-glycosylation. N-glycosylation commonly occurs through a nitrogen on an asparagine or arginine side chain, forming an N-glycosidic linkage via an amide group. O-glycosylation commonly occurs at the hydroxy oxygen of hydroxylysine, hydroxyproline, serine, tyrosine or threonine side chains, forming an 0-glycosidic linkage. GalNAc and GlcNAc are both O-linked carbohydrates. Sialic acid is found on both N- and O-linked carbohydrates.

Protein glycosylation is one of the most abundant post-translational modifications and plays a fundamental role in the control of biological systems. For example, glycosylation influences protein folding and can help to stabilize proteins and prevent their degradation. Glycosylation also can affect a protein's ability to bind to other molecules and mediate intra- or inter-cellular signaling pathways. For example, carbohydrate modifications are important for host-pathogen interactions, inflammation, development, and malignancy (Varki, A. *Glycobiology* 1993, 3, 97-130; Lasky, L. A. *Annu. Rev. Biochem.* 1995, 64, 113-139. (c) Capila, I.; Linhardt, R. J. *Angew. Chem., Int. Ed.* 2002, 41, 391-412; Rudd, P. M.; Elliott, T.; Cresswell, P.; Wilson, I. A.; Dwek, R. A. *Science* 2001, 291, 2370-2376). One such covalent modification is O-GlcNAc glycosylation, which is the covalent modification of serine and threonine residues by D-N-acetylglucosamine (Wells, L.; Vosseller, K.; Hart, G. W. *Science* 2001, 291, 2376-2378; Zachara, N. E.; Hart, G. W. *Chem. Rev.* 2002, 102, 431). The O-GlcNAc modification is found in all higher eukaryotic organisms—from *C. elegans* to man- and has been shown to be ubiquitous, inducible and highly dynamic, suggesting a regulatory role analogous to phosphorylation.

Fatty Acid Acylation

Fatty acid acylation is an enzymatic process in which fatty acids are attached to proteins in a cell. This process can affect a protein's function as well as its cellular location and is common to proteins of both cellular and viral origin (Towler et al., *Proc Natl Acad Sci USA* 1986, 83:2812-16). Myristic acid and palmitic acid are the two most common fatty acids that are attached to proteins (Olson et al., *J Biol Chem* 261(5):2458-66). Generally myristic acid is attached to soluble and membrane proteins via an amide linkage to an amino terminal glycine exposed during removal of an N-methionine residue, although it can also attach to other amino acids. Myristoylation can also occur post-translationally, for example, when a protease cleaves a polypeptide and exposes a glycine residue. Palmitic acid is attached to membrane proteins via an ester or thioester linkage. Myristoylation and palmitoylation appear to play a significant role in subcellular trafficking of proteins between membrane compartments, as well as in modulating protein-protein interactions.

Fatty acids have two distinct regions, a long hydrophobic, hydrocarbon chain and a carboxylic acid group, which is generally ionized in solution (COO—), extremely hydrophilic and readily forms esters and amides. Natural fatty acids commonly have a chain of four to 28 carbons (usually unbranched and even numbered) and may be saturated or unsaturated. Saturated fatty acids contain no double bonds in the hydrocarbon chain and include lauric acid, myristic acid, palmitic acid, stearic acid, and arachidic acid. Unsaturated fatty acids contain at least one double bond in the hydrocarbon chain and include myristolcic acid, palmitolcic acid, sapicnic acid, oleic acid, linoleic acid, α-linoleic acid, arachidonic acid, eicosapentaenoic acid, erucic acid, and docosahexaenoic acid.

Prenylation

Protein prenylation involves the attachment of an isoprenoid lipid, such as a farnesyl or a geranyl-geranyl moiety, to a C-terminal cysteine(s) of the target protein (McTaggert, *Cell Mol Life Sci* 2006, 63:255-67). These reactions are catalysed by farnesyltransferase, geranylgeranyltransferase, and Rab geranylgeranyltransferase (Magee and Seabra, *Biochem J* 2003, 376:e3-4). Due to the hydrophobic nature of the isoprenoid lipid, most prenylated proteins are associated with a membrane. Most farnesylated proteins are involved in cellular signaling where membrane association is important for function. Isoprenoid lipids are also important for mediating protein-protein binding through specialized prenyl-binding domains.

Post Translational Modifications in Viruses

Many viral proteins are extensively modified with post translational modifications, including, but not limited to glycosylation, acylation, and prenylation. In many instances, these post translational modifications are required for the virus to infect a host cell and/or evade the immune system. Post translational modifications are of particular importance in virology because, in general, viral genomes are small and thus there is heightened pressure for coding frugality. By taking advantage of a host's post translational machinery, viruses can exploit multiple pathways and function with minimal genomes, as a single post translational modification can alter a protein's function or cellular location.

For example, in HIV and Simian Immunodeficiency Viruses (SIV), glycosylation plays an important role during multiple stages of the infectivity cycle. During infection, viral glycoproteins influence the binding of viral proteins gp120 and gp41 to host cell CD4 receptor and CXCR4 and CCR5 co-receptors (Chen et al., *Virus Res* 2001, 79:91-101). Glycosylation is responsible for the proper folding and processing of gp160 (the precursor to gp 120 and gp41 (Land et al., *Biochimie* 2001, 83: 783-90) and can enhance the interactions of HIV and SIV with different cell types, including dendritic cells (Geijtenbeek et al., *Curr Top Microbiol Immunol* 2003, 276:31-54). The normal role of gp120 in HIV biology is to initiate viral binding to cells via CD4 receptor and CXCR4 and CCR5 co-receptors expressed on the target cell. When gp120 engages CD4, conformational changes occur in gp120 that expose co-receptor binding sites and trigger conformational changes in gp41. The conformational changes in gp41, in turn, expose a fusion peptide in gp41, that mediates fusion between the viral envelope and the target cell (Chen et al., *Virus Res* 2001, 79:91-101). The change of one carbohydrate at a single residue (N197) in gp120 completely changes viral tropism from CD4 tropic to CD4 independent (Kolchinksy et al., *J Virol* 2001, 75:3435-43). Changing the overall ratios of high mannose in comparison to complex type carbohydrates (sialic acid containing) present in gp120 affects the degree of viral binding to target cells (Fenouillet et al., *J Gen Virol* 1991, 1919-26). Following infection, glycosylation is required for cleavage of the envelope precursor protein (gp160) into gp120 and gp41. Upon release of the virus from an infected cell, glycosylation is also important for immune evasion as changes in envelope glycosylation significantly alter humoral immune responses to virus (Kwong et al., *Nature* 2002, 420:678-82; Shi et al., *J Gen Virol* 2005, 86:3385-96).

The acylation of viral proteins is also important to HIV biology. HIV budding is a complex process involving the coordination of many cellular and viral proteins (Resh, *Trends Microbiol* 2001, 9:57; Freed, *J Virol* 2002, 76:4679-87). HIV budding is directed to an area of the plasma membrane enriched in membrane rafts (Lindwasser et al., *J Virol* 2001, 75:7913-24; Nguyen et al., *J Virol* 2000, 74:3264-72; Ono et al., *Proc Natl Acad Sci USA* 2001, 98:13925-30; Hermida-Matsumoto et al., *J Virol* 2000, 74:8670-79), previously called lipid rafts (Pike et al., *J Lipid Res* 2006, 47:1597-98) by myristoylation of the N-terminal glycine of the capsid protein polyprotein precursor (pr55 gag) (Lindwasser et al., *J Virol* 2001, 75:7913-24; Nguyen et al., *J Virol* 2000, 74:3264-72; Ono et al., *Proc Natl Acad Sci USA* 2001, 98:13925-30). The gp120 protein is directed to membrane rafts by palmitoylation (Yang et al., *Proc Natl Acad Sci USA* 1995, 92:9871-75). Membrane rafts play an important role in several cellular processes including endocytosis, vesicle transport, cholesterol sorting, apoptosis, and signaling through the T cell receptor (Jordan et al., *J Immunol* 2003, 171:78-87; Viola et al., *Apmis* 1999, 107: 615-23; Viola et al., *Science* 1999, 283:680-82; Bezombes et al., *Curr Med Chem Anti-Canc Agents* 2002, 3:263-70; Kabouridis et al., *Eur J Immunol* 2000, 30:954-63). Direction of HIV proteins to these regions may allow the virions to more efficiently hijack these pathways, thus potentially explaining the complex pathogenicity associated with disease progression in AIDS. In fact, the removal of cholesterol, an important membrane raft component, from HIV particles results in inactivation by at least two mechanisms, a loss of the ability to fuse to the target cell and the loss of virion integrity resulting in permeabilization of the virus (Guyader et al, *J Virol* 2002, 76:10356-64; Campbell et al., *J Virol* 2004, 78:10556-65; Viard et al., *J Virol* 2002, 76:11584-595; Campbell et al., *Aids* 2002, 16:2253-61; Liao et al, *AIDS Res Hum Retroviruses* 2003, 19:675-87; Graham et al., *J Virol* 2003, 77:8237-48).

Viruses can also use the host cell machinery to modify viral proteins by adding isoprenoid lipids, such as the farnesyl and geranylgeranyl groups. For example, prenylation plays an important role in the life cycle of the hepatitis delta virus (HDV), the etiologic agent of acute and chronic liver disease associated with hepatitis B virus (Einav and Glenn, *J Antimicrobial Chemotherapy* 2003, 52:883-86). One of the HDV proteins, the large delta antigen (LHDAg), is critical for viral assembly and undergoes farnesylation in both in vitro translation systems and in intact cells (Einav and Glenn, *J. Antimicrobial Chemotherapy* 2003, 52:883-86). Inhibiting prenylation by using farnesyltransferase inhibitors prevents HDV assembly and clears HDV viremia in a mouse model of HDV, thus underscoring the importance of prenylation in the life cycle of certain viruses (Einav and Glenn, *J Antimicrobial Chemotherapy* 2003, 52:883-86).

Similar to HIV, SW, and HDV, other viruses rely on post translational modifications of viral proteins to mediate entry into host cells and/or to evade the host immune system. Thus, the alkyne-modified fatty acids, alkyne-modified carbohydrates, and alkyne-modified isoprenoid lipids described herein are expected to have a broad range of activity (such as increasing the infectivity of virus) with the result that higher titers of the virus in cell culture is achieved by virtue of increased number of viruses infecting of the cells. The cultured virus can be used in the manufacture of a vaccine against the virus.

Methods of Use

1. Method of Producing a Labeled Virus

The present disclosure provides a method of producing a virus labeled with an alkyne-modified fatty acid, an alkyne modified carbohydrate, an alkyne-modified isoprenoid lipid, or physiologically acceptable salt thereof, the method comprising contacting the virus with an alkyne-modified fatty acid, an alkyne modified carbohydrate, an alkyne-modified isoprenoid lipid, or physiologically acceptable salt, thereby producing the labeled virus.

In some embodiments, the virus is contacted with an alkyne-modified fatty acid, an alkyne modified carbohydrate, an alkyne-modified isoprenoid lipid, or physiologically acceptable salt thereof, while in other embodiments, the virus is in a cell when it is contacted with an alkyne-modified fatty acid, an alkyne modified carbohydrate, an alkyne-modified isoprenoid lipid, or physiologically acceptable salt thereof. In one embodiment, the fatty acid is one that is attached to a protein through an acylation reaction (e.g., palmitoylation or myristoylation) in a cell.

In one embodiment, the fatty acid portion of the alkyne-modified fatty acid is saturated or unsaturated and has a hydrocarbon chain with an even number of carbon atoms, such as 4-30 carbon atoms. Suitable unsaturated free fatty acids have a hydrocarbon chain with 12-24 carbon atoms and include palmitoleic acid, oleic acid, linoleic acid, alpha and gamma linolenic acid, arachidonic acid, eicosapentanoic acid and tetracosenoic acid. Suitable saturated fatty acids have a hydrocarbon chain with 4-28 carbon atoms and are preferably selected from butyric or isobutyric acid, succinic acid, caproic acid, adipic acid, caprylic acid, capric acid, lauric acid, myristic acid, palmitic acid stearic acid, and arachidic acid. It is appreciated that the alkyne-modified fatty acid, whether naturally occurring or not, may be modified by chemical substitution including, but not limited to, short chain alkylation such as methylation or acetylation, esterification, as well as other derivitisations that maintain its ability to increase viral infectivity.

In one embodiment, the alkyne-modified fatty acid is a saturated fatty acid, such as 15-ethynylpentadecanoic acid, 12-ethynyldodecanoic acid, or physiologically acceptable salt thereof. In another embodiment, the alkyne-modified fatty acid is a saturated fatty acid, such as:

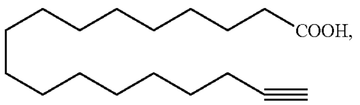

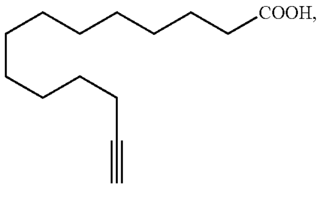

or physiologically acceptable salt thereof

In another embodiment, the alkyne-modified carbohydrate is an N-linked carbohydrate or an O-linked carbohydrate. In yet another embodiment, the alkyne-modified carbohydrate is N-ethynylacetylgalactosamine, N-ethynylacetyl-D-mannosamine, or N-ethynylacetylglucosamine. The alkyne-modified carbohydrate optionally comprises a moiety that facilitates entry into the cell including, but not limited to, a tetraacetyl moiety. Thus, in another embodiment, the alkyne-modified carbohydrate is tetraacetylated N-ethynylacetylgalactosamine, tetraacetylated N-ethynylacetyl-D-mannosamine, or tetraacetylated N-ethynylacetylglucosamine.

In another embodiment, the alkyne-modified isoprenoid lipid comprises a farnesyl group or a geranylgeranyl group and includes, but is not limited to, an ethynyl farnesyl diphosphate, an ethynyl farnesyl alcohol, an ethynyl geranylgeranyl diphosphate, or an ethynyl geranylgeranyl alcohol.

The virus may be any human animal virus, a non-human animal virus, a plant virus, an insect virus. In one embodiment, the animal is a human and the virus is a human immunodeficiency virus. In some embodiments, the virus is the human immunodeficiency virus, while in certain embodiments, the human deficiency virus is HIV-1.

2. Method of Increasing the Infectivity of a Virus

Also provided is a method of increasing the infectivity of a virus, the method comprising contacting the virus with an alkyne-modified fatty acid, an alkyne modified carbohydrate, an alkyne-modified isoprenoid lipid; or physiologically acceptable salt thereof in an amount effective to increase the infectivity of the virus.

In some embodiments, the virus is contacted with an alkyne-modified fatty acid, an alkyne modified carbohydrate, an alkyne-modified isoprenoid lipid, or physiologically acceptable salt thereof, while in other embodiments, the virus is in a cell when it is contacted with an alkyne-modified fatty acid, an alkyne modified carbohydrate, an alkyne-modified isoprenoid lipid, or physiologically acceptable salt thereof.

Certain embodiments of alkyne-modified fatty acids, alkyne-modified carbohydrates and alkyne-modified isoprenoid lipids; and viruses that can be used in this method are discussed herein.

Whether a virus labeled with an alkyne-modified fatty acid, an alkyne-modified carbohydrate, an alkyne-modified isoprenoid lipid, physiologically acceptable salt thereof is effective to treat a viral infection or other disorder in a subject can be determined using any of a variety of assays known in the art. For example, existing animal models or in vitro models of viral infection can be used to determine whether a given compound is effective to reduce viral load.

The labeled virus of the present invention may be used as a vaccine in live, attenuated form, but typically it is inactivated.

The vaccine may include whole viruses, the infectivity of which has been inactivated. Inactivated vaccine may be produced by propagating the virus in cell cultures and by purifying it from infected cells and culture media by high-speed centrifugation in a density gradient formed by sucrose or other high-density media. Alternatively, the virus may be purified by chromatography. The infectivity of the purified viruses is destroyed by inactivating the viruses by chemical treatment (e.g. formalin inactivation like that used to produce inactivated polio virus vaccine), irradiation or heat treatment.

Attenuated viruses are viruses of which the virulence has been reduced. Growth behavior is recognized as an indicator for virus attenuation. Generally, a virus strain is regarded as attenuated if it has lost its capacity or only has reduced capacity to reproductively replicate in host cells. Attenuation may be carried out by different methods including serial passage of the virus in cell cultures, antigenic modification by chemical treatments, construction of recombinant or chimeric viruses, mutagenization of viral genome, deletion or insertion of certain gene regions, selection of temperature sensitive mutants or irradiation. Alternatively, the labeled viruses of the present invention may be attenuated natural virus isolates or infectious virus cDNA or RNA having reduced capability to cause clinical disease.

The labeled viruses of the present invention when used as a vaccine can be propagated in cell culture systems. The cells used for virus/vaccine production may be cell lines, for example, cells that grow continuously in vitro, either as single-cell suspension culture in bioreactors or as a monolayer on a cell-support surface of tissue culture flasks or roller-bottles. Some examples for cell lines used for the production of viruses are: the human fetal lung cell-line MRC-5 used for the manufacture of polio viruses and the human fetal lung cell-line WI-38 used for the manufacture of measles virus, mumps virus and rubella virus (MMR II) (Merck Sharp & Dohme).

Primary animal cells may also be used for the manufacture of vaccines. An example of primary cells that are used for virus production are chicken embryo fibroblasts (CEF cells). These cells are used for the production of measles and Japanese encephalitis virus (Pasteur Merieux), mumps virus (manufactured by Provaccine), rabies virus (manufactured by Chiron Berhing GmbH & Co.), yellow fever virus (manufactured by Aprilvax), influenza virus (manufactured by Wyeth Labs and SmithKline & Beecham) and modified Vaccinia virus Ankara (MVA).

CEF cells are often used because many virus vaccines are made by attenuating the virulent disease-causing virus by serially passaging in CEF cells. Attenuated viruses are preferably not propagated on human cells since there is a concern that the viruses might become replication competent in cells of human origin. Viruses that have regained the ability to replicate in human cells represent a health risk if administered to humans, in particular if the individuals are immune compromised.

3. Method of Increasing the Infectivity of a Virus for Use In Vitro Transfection and In Vivo Gene Therapy Also provided is a method of increasing the infectivity of a transfection virus, the method comprising contacting the virus with an alkyne-modified fatty acid, an alkyne-modified carbohydrate, an alkyne-modified isoprenoid lipid, or physiologically acceptable salt thereof in an amount effective to increase the infectivity of the virus. In some embodiments, the virus is contacted with an alkyne-modified fatty acid, an alkyne modified carbohydrate, an alkyne-modified isoprenoid lipid, or physiologically acceptable salt thereof, while in other embodiments, the virus is in a cell when it is contacted with an alkyne-modified fatty acid, an alkyne modified carbohydrate, an alkyne-modified isoprenoid lipid, or physiologically acceptable salt thereof.

Certain embodiments of alkyne-modified fatty acids, alkyne-modified carbohydrates and alkyne-modified isoprenoid lipids; and the viruses that can be used in this method are discussed herein.

Whether the virus labeled with an alkyne-modified fatty acid, alkyne-modified carbohydrate, alkyne-modified isoprenoid lipid, or physiologically acceptable salt thereof is effective to increase the infectivity of a virus can be determined using any of a variety of assays known in the art.

The labeled virus of the present invention because of its increased infectivity may be used in vivo as a viral vector for gene therapy to introduce an exogenous gene into a whole organism, such as a human animal, non-human animal, insect or plant. The labeled virus of the present invention may be also used in vitro as a viral vector for transfection, that is, to introduce into a cell a foreign gene for expression in a human animal, non-human animal, insect or plant cell.

Standard techniques in molecular biology can be used to generate the labeled viruses provided herein which can express a non-viral gene. Such techniques include various nucleic acid manipulation techniques, nucleic acid transfer protocols, nucleic acid amplification protocols, and other molecular biology techniques known in the art. For example, point mutations can be introduced into a gene of interest through the use of oligonucleotide mediated site-directed mutagenesis.

The methods of the present invention can be used to provide a labeled virus of the present invention, either before or after introduction of an exogenous gene into the virus. Exemplary exogenous gene products include, but without limitation, proteins and RNA molecules.

The labeled viruses of the present invention can express in a host cell a detectable gene product, a therapeutic gene product, a gene product for manufacturing or harvesting, or an antigenic gene product for antibody harvesting.

Such host cells can be a group of a single type of cells or a mixture of different types of cells. Host cells can include cultured cell lines, primary cells and proliferative cells. These host cells can include any of a variety of human animal cells or non-human animal cells, such as mammalian, avian and insect cells and tissues that are susceptible to infection by the labeled virus of the present invention, such as, for example, chicken embryo, rabbit, hamster and monkey kidney cells. Suitable host cells include but are not limited to hematopoietic cells (totipotent, stem cells, leukocytes, lymphocytes, monocytes, macrophages, APC, dendritic cells, non-human cells and the like), pulmonary cells, tracheal cells, hepatic cells, epithelial cells, endothelial cells, muscle cells (e.g., skeletal muscle, cardiac muscle or smooth muscle), fibroblasts, and cell lines including, for example, CV-1, BSC40, Vero, BSC40 and BSC-1, and human HeLa cells. Methods for transfecting these host cells, phenotypically selecting transformants, and other such methods are known in the art.

The labeled viruses of the present invention can be used to modify an organism to express an exogenous gene, the modification of which can also contain one or more regulatory sequences to regulate expression of the exogenous gene. As is known in the art, regulatory sequences can permit constitutive expression of the exogenous gene or can permit inducible expression of the exogenous gene. Further, the regulatory sequence can permit control of the level of expression of the exogenous gene.

Labeled Viruses

Also provided is a labeled virus comprising an alkyne-modified fatty acid moiety, an alkyne-modified carbohydrate moiety or an alkyne-modified isoprenoid lipid moiety. In some embodiments, these moieties are non-naturally occurring.

In some embodiments, the alkyne-modified carbohydrate moiety comprises a carbohydrate which can be selected from a wide variety of carbohydrates commercially available and/or widely known to those skilled in the art. In some embodiments, the carbohydrate may be naturally occurring.

It is appreciated that the alkyne-modified carbohydrate moiety, whether naturally occurring or not, may be modified, for example, by short chain alkylation such as methylation or acetylation, esterification, as well as other derivatizations that maintain the ability to increase the infectivity of the virus.

In one embodiment, the alkyne-modified carbohydrate moiety contains another moiety that facilitates entry into the cell including, but not limited to, one or more acetyl moieties. Thus, in one embodiment, the carbohydrate of alkyne-modified carbohydrate moiety is a tetraacetylated version of an N-linked carbohydrate or an O-linked carbohydrate. In yet another embodiment, the alkyne-modified carbohydrate moiety may be comprised of tetraacetylated N-azidoacetylgalactosamine, tetraacetylated N-azidoacetyl-D-mannosamine, or tetraacetylated N-azidoacetylglucosamine.

In one embodiment, the alkyne-modified carbohydrate moiety may be one that is attached directly or indirectly to a protein through a glycosylation reaction in a cell. In one embodiment, the alkyne-modified carbohydrate may be an N-linked carbohydrate or an O-linked carbohydrate moiety. In yet another embodiment, the alkyne modified carbohydrate may be N-ethynylacetylgalactosamine moiety, N-ethynylacetyl-D-mannosamine moiety, or N-ethynylacetylglucosamine moiety.

In some embodiments, the alkyne-modified fatty acid moiety comprises a fatty acid. The fatty acid may be selected from a wide variety of fatty acids commercially available and/or widely known to those skilled in the art. In some embodiments, the fatty acid may be selected to prevent, inhibit and/or retard viral infection of cells. In some embodiments, the fatty acid may be naturally occurring.

In one embodiment, the fatty acid may be a saturated or unsaturated and has a hydrocarbon chain with an even number of carbon atoms, such as 4-30 carbon atoms. Suitable unsaturated fatty acids have a hydrocarbon chain with 12-24 carbon atoms and may be selected from palmitoleic acid, oleic acid, linoleic acid, alpha and gamma linolenic acid, arachidonic acid, eicosapentanoic acid and tetracosenoic acid. Suitable saturated fatty acids have a hydrocarbon chain with 4-28 carbon atoms and may be selected from butyric or isobutyric acid, succinic acid, caproic acid, adipic acid, caprylic acid, capric acid, lauric acid, myristic acid, In addition, it is possible to replace the fatty acid in the alkyne-modified moiety with an alkyne, ketone, or other small molecule that has been shown to be metabolically compatible palmitic acid stearic acid, and arachidic acid. It is appreciated that the alkyne-containing fatty acid moiety, whether naturally occurring or not, may be modified by chemical substitution including, but not limited to, short chain alkylation such as methylation or acetylation, esterification, as well as other derivitisations that maintain the ability to increase the infectivity of the virus.

In one embodiment, the alkyne-modified fatty acid moiety is a saturated fatty acid moiety, such as 15-ethynylpentadecanyl or 12-ethynyldodecanyl. In another embodiment, the alkyne-modified fatty acid is a saturated fatty acid moiety, such as:

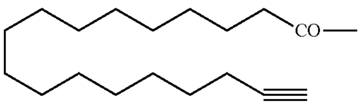

or

-continued

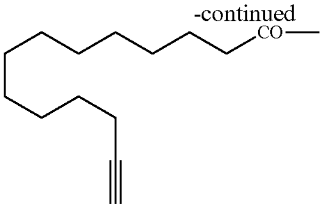

In one embodiment, the alkyne modified fatty acid moiety is one that may attached to a protein of the virus through an acylation reaction (e.g., palmitoylation or myristoylation) in a cell.

In some embodiments, the virus may be any human animal virus, a non-human animal virus, a plant virus, an insect virus. In some embodiments, the virus is a human immunodeficiency virus. In certain embodiments, the human immunodeficiency virus is HIV-1.

Viruses

The alkyne-modified fatty acids, alkyne-modified carbohydrates, or alkyne-modified isoprenoid lipids target post translational modifications common to most viruses and thus represent a new class of agents with potential for increasing the infectivity of a broad spectrum of viruses. In principle, these compounds may be used to increase the infectivity of a human animal virus, a non-human animal virus, a plant virus, or insect virus. In some embodiments, the virus is a plant virus. In some embodiments, the virus is an insect virus. In other embodiments, the virus is an non-human animal virus. In yet other embodiments, the virus is a human animal virus. In one embodiment, the virus is one that infects a non-human mammal, such as a mammalian livestock animal, including, but not limited to, a cow, a horse, a pig, a goat, or a sheep.

In other embodiments, the virus is a DNA virus. DNA viruses include, but are not limited to a virus belonging to one of the following families: adenovirus, astrovirus, hepadnavirus, herpesvirus, papovavirus, and poxvirus. In other embodiments, the virus is an RNA virus. RNA viruses include but are not limited to a virus belonging to one the following families: arenavirus, bunyavirus, calcivirus, coronavirus, filovirus, flavivirus, orthomyxovirus, paramyxovirus, picornavirus, reovirus, retrovirus, rhabdovirus, and togavirus.

1. Non-Human Animal Viruses

In methods of the present invention directed to a non-human animal, the non-human animal virus may be selected from a picornavirus, such as a bovine enterovirus, a porcine enterovirus B, a foot-and-mouth disease virus, an equine rhinitis A virus, a bovine rhinitis B virus, a ljungan virus, equine rhinitis B virus, an aichi virus, a bovine kobuvirus, a porcine teschovirus, a porcine sapelovirus, a simian sapelovirus, an avian sapelovirus, an avian encephalomyelitis virus, a duck hepatitis A virus, or a simian enterovirus A; a pestivirus, such as border disease virus, a bovine virus diarrhea, or a classical swine fever virus; an arterivirus, such as an equine arteritis virus, a porcine reproductive and respiratory syndrome virus, a lactate dehydrogenase elevating virus, or a simian haemorrhagic fever virus; a coronavirus, such as a bovine coronavirus, a porcine coronavirus, a feline coronavirus, or a canine coronavirus; a paramyxovirus, such as a hendra virus, a nipah virus, a canine distemper virus, a rinderpest virus, a Newcastle disease virus, and a bovine respiratory syncytial virus; an orthomyxovirus, such as an influenza A virus, an influenza B virus, or an influenza C virus; a reovirus, such as a bluetongue virus; a porcine circovirus, a herpesvirus, such as a pseudorabies virus or a bovine herpesvirus 1; an asfarvirus, such as an African swine fever virus; a retrovirus, such as a simian immunodeficiency virus, a feline immunodeficiency virus, a bovine immunodeficiency virus, a bovine leukemia virus, a feline leukemia virus, a Jaagsiekte sheep retrovirus, or a caprine arthritis encephalitis virus; aflavivirus, such as a yellow fever virus, a West Nile virus, a dengue fever virus, a tick borne encephalitis virus, or a bovine viral diarrhea; or a rhabdovirus, such as a rabies virus.

2. Human Animal Viruses

In methods of the present invention directed to human animals, the human animal virus may be selected from an adenovirus, an astrovirus, a hepadnavirus, a herpesvirus, a papovavirus, a poxvirus, an arenavirus, a bunyavirus, a calcivirus, a coronavirus, a filovirus, a flavivirus, an orthomyxovirus, a paramyxovirus, a picornavirus, a reovirus, a retrovirus, a rhabdovirus, or a togavirus.

In some embodiments, the adenovirus includes, but is not limited to, a human adenovirus. In some embodiments, the astrovirus includes, but is not limited to, a mamastrovirus. In some embodiments, the hepadnavirus includes, but is not limited to, the hepatitis B virus. In some embodiments, the herpesvirus includes, but is not limited to, a herpes simplex virus type I, a herpes simplex virus type 2, a human cytomegalovirus, an Epstein-Barr virus, a varicella zoster virus, a roseolovirus, and a Kaposi's sarcoma-associated herpesvirus. In some embodiments, the papovavirus includes, but is not limited to, human papilloma virus and a human polyoma virus. In some embodiments, the poxvirus includes, but is not limited to, a variola virus, a vaccinia virus, a cowpox virus, a monkeypox virus, a smallpox virus, a pseudocowpox virus, a papular stomatitis virus, a tanapox virus, a yaba monkey tumor virus, and a molluscum contagiosum virus. In some embodiments, the arenavirus includes, but is not limited to lymphocytic choriomeningitis virus, a lassa virus, a machupo virus, and a junin virus. In some embodiments, the bunyavirus includes, but is not limited to, a hanta virus, a nairovirus, an orthobunyavirus, and a phlebovirus. In some embodiments, the calcivirus includes, but is not limited to, a vesivirus, a norovirus, such as the Norwalk virus and a sapovirus. In some embodiments, the coronavirus includes, but is not limited to, a human coronavirus (etiologic agent of severe acute respiratory syndrome (SARS)). In some embodiments, the filovirus includes, but is not limited to, an Ebola virus and a Marburg virus. In some embodiments, the flavivirus includes, but is not limited to, a yellow fever virus, a West Nile virus, a dengue fever virus, a hepatitis C virus, a tick borne encephalitis virus, a Japanese encephalitis virus, a Murray Valley encephalitis virus, a St. Louis encephalitis virus, a Russian spring-summer encephalitis virus, a Omsk hemorrhagic fever virus, a bovine viral diarrhea virus, a Kyasanus Forest disease virus, and a Powassan encephalitis virus. In some embodiments, the orthomyxovirus includes, but is not limited to, influenza virus type A, influenza virus type B, and influenza virus type C. In some embodiments, the paramyxovirus includes, but is not limited to, a parainfluenza virus, a rubula virus (mumps), a morbillivirus (measles), a pneumovirus, such as a human respiratory syncytial virus, and a subacute sclerosing panencephalitis virus. In some embodiments, the picornavirus includes, but is not limited to, a poliovirus, a rhinovirus, a coxsackievirus A, a coxsackievirus B, a hepatitis A virus, an echovirus, and an eneterovirus. In some embodiments, the reovirus includes, but is not limited to, a Colorado tick fever virus and a rotavirus. In some embodiments, the retrovirus includes, but is not limited to, a lentivirus, such as a human immunodeficiency virus, and a human T-lymphotrophic virus (HTLV). In some embodiments, the rhabdovirus includes, but is not limited to, a lyssavirus, such as the rabies virus, the vesicular stomatitis virus and the infectious hematopoietic necrosis virus. In some embodiments, the togavirus includes, but is not limited to, an alphavirus, such as a Ross river virus, an O'nyong'nyong virus, a Sindbis virus, a Venezuelan equine encephalitis virus, an Eastern equine encephalitis virus, and a Western equine encephalitis virus, and a rubella virus.

3. Plant Viruses

In methods of the present invention directed to a plant, the plant virus may be selected from an alfamovirus, an allexivirus, an alphacryptovirus, an anulavirus, an apscaviroid, an aureusvirus, an avenavirus, an aysunviroid, a badnavirus, a begomovirus, a benyvirus, a betacryptovirus, a betaflexiviridae, a bromovirus, a bymovirus, a capillovirus, a carlavirus, a carmovirus, a caulimovirus, a cavemovirus, a cheravirus, a closterovirus, a cocadviroid, a coleviroid, a comovirus, a crinivirus, a cucumovirus, a curtovirus, a cytorhabdovirus, a dianthovirus, an enamovirus, an umbravirus & B-type satellite virus, a fabavirus, a fijivirus, a furovirus, a hordeivirus, a hostuviroid, an idaeovirus, an ilarvirus, an ipomovirus, a luteovirus, a machlomovirus, a macluravirus, a marafivirus, a mastrevirus, a nanovirus, a necrovirus, a nepovirus, a nucleorhabdovirus, an oleavirus, an ophiovirus, an oryzavirus, a panicovirus, a pecluvirus, a petuvirus, a phytoreovirus, a polerovirus, a pomovirus, a pospiviroid, a potexvirus, a potyvirus, a reovirus, a rhabdovirus, a rymovirus, a sadwavirus, a SbCMV-like virus, a sequivirus, a sobemovirus, a tenuivirus, a TNsatV-like satellite virus, a tobamovirus, a topocuvirus, a tospovirus, a trichovirus, a tritimovirus, a tungrovirus, a tymovirus, an umbravirus, a varicosavirus, a vitivirus, or a waikavirus.

4. Insect Viruses

In methods of the present directed to an insect virus, the insect virus may be selected from a densovirus, such as *Junonia coenia* densovirus, *Bombyx mori* densovirus, *Aedes aegypti* densovirus, or *Penplanta fuliginosa* densovirus; an iridovirus, such as iridescent virus 6; a chloriridovirus, a baculovirus, such as nuclear polyhedrosis virus or a granulovirus; a polydnavirus, such as a ichnovirus or a bracovirus; an entomopox virus, such as an entomopox A virus, an entomopox B virus, or an entomopox C virus; an ascovirus, such as a *Spodoptera frugiperda* ascovirus 1a, a *Trichoplusia ni* ascovirus 2a, or a *Diadromus pulchellus* ascovirus 4a; an insect picornavirus, such as a bee acute paralysis virus, a *Drosophila* P, C, or A virus, a bee virus X virus, or a silkworm flacherie virus; a calicivirus; a nodavirus, such as a black beetle virus, a flock house virus, a nodamura virus, a pariacoto virus, or a gypsy moth virus.

Combination Therapy

In one embodiment, a pharmaceutical composition comprising a virus comprising an alkyne-modified fatty acid moiety, an alkyne-modified carbohydrate moiety or an alkyne-modified isoprenoid lipid moiety, and at least one anti-viral agent may be administered in combination therapy. In some embodiments, the labeled virus may be inactivated or attenuated. The therapy is useful for treating viral infections, including, but not limited to, an HIV infection. The term "in combination" in this context means that the virus comprising an alkyne-modified fatty acid, alkyne-modified carbohydrate, the alkyne-modified isoprenoid lipid, or combination thereof, and the anti-viral agent are given substantially contemporaneously, either simultaneously or sequentially. In one embodiment, if given sequentially, at the onset of administration of the second, the first of the two is still detectable at effective concentrations at the site of treatment. In another embodiment, if given sequentially, at the onset of administration of the second, the first of the two is not detectable at effective concentrations at the site of treatment.

For example, the combination therapy can include a virus comprising an alkyne-modified fatty acid moiety, an alkyne-modified carbohydrate moiety, or an alkyne-modified isoprenoid lipid moiety co-formulated with, and/or co-administered with, at least one additional anti-viral agent. Although specific examples of anti-viral agents are provided, in principle, the labeled virus can be combined with any pharmaceutical composition useful for treating a viral infection. Such combination therapies may advantageously use lower dosages of the administered agents, thus avoiding possible toxicities or complications associated with the various monotherapies. Moreover, the additional anti-viral agents disclosed herein act on pathways or stage of viral infection in addition to or that differ from the pathway stage of viral infection affected by the labeled virus, and thus are expected to enhance and/or synergize with the effects of the labeled virus. The additional anti-viral agent may include at least one reverse transcriptase inhibitor, a virus protease inhibitor, a viral fusion inhibitor, a viral integrase inhibitor, a glycosidase inhibitor, a viral neuraminidase inhibitor, an M2 protein inhibitor, an amphotericin B, hydroxyurea, α-interferon, β-interferon, γ-interferon, and an antisense oligonucleotide.

The at least one reverse transcriptase inhibitor includes, but is not limited to, one or more nucleoside analogs, such as Zidovudine (AZT), Didanosine (ddI), Zalcitabine (ddC), Stavudine (d4T), Lamivudine (3TC), Abacavir (ABC), Emtricitabine (FTC), Entecavir (INN), Apricitabine (ATC), Atevirapine, ribavirin, acyclovir, famciclovir, valacyclovir, ganciclovir, and valganciclovir; one or more nucleotide analogs, such as Tenofovir (tenofovir disoproxil fumarate), Adefovir (bis-POM PMPA), PMPA, and cidofovir; or one or more non-nucleoside reverse transcriptase inhibitors, such as Efavirenz, Nevirapine, Delavirdine, and Etravirine.

The at least one viral protease inhibitor includes, but is not limited to, tipranavir, darunavir, indinavir, lopinavir, fosamprenavir, atazanavir, saquinavir, ritonavir, indinavir, nelfinavir, and amprenavir.

The at least one viral fusion inhibitor includes, but is not limited to a CD4 antagonist, such as soluble CD4 or an antibody that binds to CD4, such as TNX-355, BMS-806; a CCR5 antagonist, such as SCH-C, SCH-D, UK-427,857, maraviroc, vicriviroc, or an antibody that binds to CCR5, such as PRO-140; a CXCR4 antagonist, such as, AMD3100 or AMD070; or an antagonist of gp41, such as enfuvirtide.

The at least one viral integrase inhibitor includes, but is not limited to, raltegravir.

The at least one glycosidase inhibitor includes, but is not limited to, SC-48334 or MDL-28574.

The at least one viral neuraminidase inhibitor includes, but is not limited to, oseltamivir, peramivir, zanamivir, and laninamivir. Neuraminidase is a protein on the surface of influenza viruses that mediates the virus' release from an infected cell. (Bossart-Whitaker et al., *J Mol Biol,* 1993, 232:1069-83). The influenza virus attaches to the cell membrane using the viral hemagglutinin protein. The hemagglutinin protein binds to sialic acid moieties found on glycoproteins in the host cell's membranes. In order for the virus to be released from the cell, neuraminidase must enzymatically cleave the sialic acid groups from the host glycoproteins. Thus, inhibiting neuraminidase prevents the release of the influenza virus from an infected cell.

The at least one M2 inhibitor includes, but is not limited to, amantadine and rimantadine. M2 is an ion channel protein found in the viral envelope of the influenza virus (Henckel et al., *J Biol Chem,* 1998, 273:6518-24). The M2 protein plays an important role in controlling the uncoating of the influenza virus, leading to the release of the virion contents into the host cell cytoplasm. Blocking M2 inhibits viral replication.

A virus comprising an alkyne-modified fatty acid moiety, an alkyne-modified carbohydrate moiety or an alkyne-modified isoprenoid lipid moiety disclosed herein can be used in combination with other therapeutic agents to treat specific viral infections as discussed in further detail below.

Non-limiting examples of agents for treating an HIV infection, include, but are not limited to, this virus modified so that it comprises an alkyne-modified fatty acid moiety, an alkyne-modified carbohydrate moiety, or an alkyne-modified isoprenoid lipid moiety e combined with at least one of the following: Zidovudine (AZT), Didanosine (ddI), Zalcitabine (ddC), Stavudine (d4T), Lamivudine (3TC), Abacavir (ABC), Emtricitabine (FTC), Entecavir (INN), Apricitabine (ATC), Tenofovir (tenofovir disoproxil fumarate), Adefovir (bis-POM PMPA) Efavirenz, Nevirapine, Delavirdine, Etravirine, tipranavir, darunavir, indinavir, lopinavir, fosamprenavir, atazanavir, saquinavir, ritonavir, indinavir, nelfinavir, amprenavir, a CD4 antagonist, such as soluble CD4 or an antibody that binds to CD4, such as TNX-355, BMS-806, a CCR5 antagonist, such as SCH-C, SCH-D, UK-427,857, maraviroc, vicriviroc, or an antibody that binds to CCR5, such as PRO-140, a CXCR4 antagonist, such as, AMD3100 or AMD070, or an antagonist of gp41, such as enfuvirtide.

Specific examples of combination therapy that can be used to treat HIV infection include, but are not limited to, this virus modified so that it comprises an alkyne-modified fatty acid moiety, an alkyne-modified carbohydrate moiety, or an alkyne-modified isoprenoid lipid moiety combined with: 1) tenofovir, emtricitabine, and efavirenz; 2) lopinavir and ritonavir; 3) lamivudine and zidovudine; 4) abacavir, lamivudine, and zidovudine; 5) lamivudine and abacavir; or 6) tenofovir and emtricitabine.

Non-limiting examples of agents for treating a herpesvirus infection include, but are not limited to, this virus modified so that it comprises an alkyne-modified fatty acid moiety, an alkyne-modified carbohydrate moiety, or an alkyne-modified isoprenoid lipid moiety combined with acyclovir, famciclovir, valacyclovir, cidofovir, foscarnet, ganciclovir, and valganciclovir.

Non-limiting examples of agents for treating an influenza virus infection include, but are not limited to, this virus modified so that it comprises an alkyne-modified fatty acid moiety, an alkyne-modified carbohydrate moiety, or an alkyne-modified isoprenoid lipid moiety combined with amantadine, rimantadine, oseltamivir, peramivir, zanamivir, and laninamivir.

Non-limiting examples of agents for treating a respiratory syncitial virus infection include, but is not limited to, this virus modified so that it comprises an alkyne-modified fatty acid moiety, an alkyne-modified carbohydrate moiety, or an alkyne-modified isoprenoid lipid moiety combined with ribavirin.

Another aspect of the present invention accordingly relates to kits for carrying out the combined administration of a virus comprising an alkyne-modified fatty acid moiety, an alkyne-modified carbohydrate moiety or an alkyne-modified isoprenoid lipid moiety with other therapeutic agents. In one embodiment, the kit comprises the virus comprising an alkyne-modified fatty acid moiety, an alkyne-modified carbohydrate moiety or an alkyne-modified isoprenoid lipid moiety formulated in a pharmaceutical excipient, and at least one anti-viral agent, formulated as appropriate in one or more separate pharmaceutical preparations.

Compositions and Methods of Administration

Also provided are compositions that are suitable for pharmaceutical use and administration to patients. The compositions comprise virus comprising an alkyne-modified fatty acid moiety, an alkyne-modified carbohydrate moiety or an alkyne-modified isoprenoid lipid moiety, or any of the viruses herein.

In some embodiments, the composition comprises a virus comprising an alkyne-modified fatty acid moiety, an alkyne-modified carbohydrate moiety or an alkyne-modified isoprenoid lipid moiety, wherein the virus is inactivated. In some embodiments, the composition comprises a virus comprising an alkyne-modified fatty acid moiety, an alkyne-modified carbohydrate moiety or an alkyne-modified isoprenoid lipid moiety, wherein the virus is attenuated.

In some embodiments, the composition further comprise a pharmaceutically acceptable excipient.

In some embodiments, the composition comprises a virus comprising an alkyne-modified fatty acid moiety, an alkyne-modified carbohydrate moiety or an alkyne-modified isoprenoid lipid moiety, wherein the virus is a naturally occurring virus. In some embodiments, the composition comprises a virus comprising an alkyne-modified fatty acid moiety, an alkyne-modified carbohydrate moiety or an alkyne-modified isoprenoid lipid moiety, wherein the virus is a non-naturally occurring virus.

In one embodiment, the alkyne modified fatty acid moiety comprises a fatty acid which may be a saturated or unsaturated and has a hydrocarbon chain with an even number of carbon atoms, such as 4-30 carbon atoms. Suitable unsaturated fatty acids have a hydrocarbon chain with 12-24 carbon atoms and may be selected from palmitoleic acid, oleic acid, linoleic acid, alpha and gamma linolenic acid, arachidonic acid, eicosapentanoic acid and tetracosenoic acid. Suitable saturated fatty acids have a hydrocarbon chain with 6-28 carbon atoms and may be selected from butyric or isobutyric acid, succinic acid, caproic acid, adipic acid, caprylic acid, capric acid, lauric acid, myristic acid, In addition, it is possible to replace the fatty acid in the alkyne-modified moiety with an alkyne, ketone, or other small molecule that has been shown to be metabolically compatible palmitic acid stearic acid, and arachidic acid. It is appreciated that the alkyne-containing fatty acid moiety, whether naturally occurring or not, may be modified by chemical substitution including, but not limited to, short chain alkylation such as methylation or acetylation, esterification, as well as other derivitisations that maintain the ability to increase the infectivity of the virus.

In one embodiment, the alkyne-modified fatty acid moiety is a saturated fatty acid moiety, such as 15-ethynylpentadecanyl or 12-ethynyldodecanyl. In another embodiment, the alkyne-modified fatty acid is a saturated fatty acid moiety, such as:

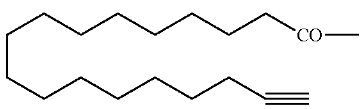

or

-continued

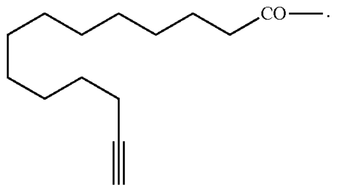

The pharmaceutical compositions may also be included in a container, pack, or dispenser together with instructions for administration.

A composition of the present invention may be formulated to be compatible with its intended route of administration. Methods to accomplish the administration are known to those of ordinary skill in the art. The compositions may be topically or orally administered, or capable of transmission across mucous membranes. Examples of administration of a composition include oral ingestion or inhalation. Administration may also be intravenous, intraperitoneal, intramuscular, intracavity, subcutaneous, cutaneous, or transdermal.

Solutions or suspensions used for intradermal or subcutaneous application typically include at least one of the following components: a sterile diluent such as water, saline solution, fixed oils, polyethylene glycol, glycerine, propylene glycol, or other synthetic solvent; antibacterial agents such as benzyl alcohol or methyl parabens; antioxidants such as ascorbic acid or sodium bisulfite; chelating agents such as ethylenediaminetetraacetic acid (EDTA); buffers such as acetate, citrate, or phosphate; and tonicity agents such as sodium chloride or dextrose. The pH can be adjusted with acids or bases. Such preparations may be enclosed in ampoules, disposable syringes, or multiple dose vials.

Solutions or suspensions used for intravenous administration include a carrier such as physiological saline, bacteriostatic water, CREMOPHOR EL (BASF, Parsippany, N.J.), ethanol, or polyol. In all cases, the composition must be sterile and fluid for easy syringability. Proper fluidity can often be obtained using lecithin or surfactants. The composition must also be stable under the conditions of manufacture and storage. Prevention of microorganisms can be achieved with antibacterial and antifungal agents, e.g., parabens, chlorobutanol, phenol, ascorbic acid, thimerosal, etc. In many cases, isotonic agents (sugar), polyalcohols (mannitol and sorbitol), or sodium chloride may be included in the composition. Prolonged absorption of the composition can be accomplished by adding an agent which delays absorption, e.g., aluminum monostearate and gelatin.

Oral compositions include an inert diluent or edible carrier. The composition can be enclosed in gelatin or compressed into tablets. For the purpose of oral administration, the composition comprising a virus comprising an alkyne-modified fatty acid moiety, an alkyne-modified carbohydrate moiety or an alkyne-modified isoprenoid lipid moiety can be incorporated with excipients and placed in tablets, troches, or capsules. Pharmaceutically compatible binding agents or adjuvant materials can be included in the composition. The tablets, troches, and capsules, may contain (1) a binder such as microcrystalline cellulose, gum tragacanth or gelatin; (2) an excipient such as starch or lactose, (3) a disintegrating agent such as alginic acid, Primogel, or corn starch; (4) a lubricant such as magnesium stearate; (5) a glidant such as colloidal silicon dioxide; or (6) a sweetening agent or a flavoring agent.

The composition may also be administered by a transmucosal or transdermal route. Transmucosal administration can be accomplished through the use of lozenges, nasal sprays, inhalers, or suppositories. Transdermal administration can also be accomplished through the use of a composition containing ointments, salves, gels, or creams known in the art. For transmucosal or transdermal administration, penetrants appropriate to the barrier to be permeated are used.

For administration by inhalation, the virus comprising an alkyne-modified fatty acid moiety, an alkyne-modified carbohydrate moiety, or an alkyne-modified isoprenoid lipid moiety are delivered in an aerosol spray from a pressured container or dispenser, which contains a propellant (e.g., liquid or gas) or a nebulizer. In certain embodiments, the virus is prepared with a carrier to protect the compounds against rapid elimination from the body. Biodegradable polymers (e.g., ethylene vinyl acetate, polyanhydrides, polyglycolic acid, collagen, polyorthoesters, polylactic acid) are often used. Methods for the preparation of such formulations are known by those skilled in the art.

In other embodiments, the composition comprises a delivery agent for delivering the virus comprising an alkyne-modified fatty acid moiety, the alkyne-modified carbohydrate moiety or an alkyne-modified isoprenoid lipid moiety to a cell including but not limited to, a liposome. Liposomes (also known as lipid vesicles) are colloidal particles that are prepared from polar lipid molecules derived either from natural sources or chemical synthesis. Such spherical, closed structures composed of curved lipid bilayers, are typically used to entrap drugs, which are often cytotoxic, in order to reduce toxicity and/or increase efficacy. Liposome-entrapped drug preparations are often provided in a dry (e.g. freeze-dried) form, which is subsequently reconstituted with an aqueous solution immediately prior to administration. This is done in order to minimize the possibility of leakage of e.g. cytotoxic drug into aqueous solution and thereby reducing the entrapping effect of the liposome.

Examples of formulations comprising inter alia liposome-encapsulated active ingredients are discussed in U.S. Pat. Nos. 4,427,649, 4,522,811, 4,839,175, 5,569,464, EP 249 561, WO 00/38681, WO 88/01862, WO 98/58629, WO 98/00111, WO 03/105805, U.S. Pat. Nos. 5,049,388, 5,141,674, 5,498,420, 5,422,120, WO 87/01586, WO 2005/039533, US 2005/0112199 and U.S. Pat. No. 6,228,393, all of which are hereby incorporated by reference in their entirety.

The virus comprising an alkyne-modified fatty acid moiety, an alkyne-modified carbohydrate moiety or an alkyne-modified isoprenoid lipid moiety containing compositions are administered in therapeutically effective amounts as described. Therapeutically effective amounts may vary with the subject's age, condition, sex, and severity of medical condition. Appropriate dosage may be determined by a physician based on clinical indications. The virus comprising an alkyne-modified fatty acid moiety, an alkyne-modified carbohydrate moiety or an alkyne-modified isoprenoid lipid moiety containing composition may be given as a bolus dose to maximize the circulating levels of the virus for the greatest length of time. Continuous infusion may also be used after the bolus dose.

Compositions comprising a virus comprising an alkyne-modified fatty acid moiety, an alkyne-modified carbohydrate moiety or an alkyne-modified isoprenoid lipid moiety, wherein the virus is inactivated, can be given parenterally by injections, perorally, intradermally, transcutaneously, sublingually, intranasally, as inhalation, or per rectum. Each immunizing dose includes viral structures in a titer, which is able to induce proper immune response in a human animal or a non-human animal. This dose may correspond to that used in Salk-type inactivated poliovirus vaccine including 1.8-2 μg of viral protein per each dose and 20-40 antigenic D-units of poliovirus type 1, 4-8 antigenic D-units of poliovirus type 2 and 16-32 antigenic D-units of poliovirus type 3. The dose may also be another, if it has been confirmed to be safe and immunogenic or able to stimulate the immune system Compositions comprising a virus comprising an alkyne-modified fatty acid moiety, an alkyne-modified carbohydrate moiety or an alkyne-modified isoprenoid lipid moiety, wherein the virus is attenuated, may conveniently formulated into a mucosal composition, which may be given perorally, sublingually, intranasally, as inhalation, or per rectum. In some embodiments, it is administered orally. Each immunizing dose includes infective viruses or infective RNA or cDNA in a titer, which is able to produce infection or activation of the innate or adaptive immune system or induce regulatory T-cells or regulatory cytokines in humans. This dose may correspond to that which is used in the traditional Sabin-type live oral poliovirus vaccine including a minimum of $10^{5.5}$-$10^{6}$ $TCID_{50}$ for poliovirus Type 1, $10^{5}$ $TCID_{50}$ for poliovirus type 2 and $10^{5.5}$-$10^{5.8}$ $TCID_{50}$ for poliovirus type 3 live attenuated Sabin strains of polioviruses. The dose may also be another, if it has been confirmed to be safe and infectious or able to activate the innate or adaptive immune system. (TCID=tissue culture infectious dose; $TCID_{50}$=the dose which infects 50% of the cultures.)

In certain circumstances, it may be advantageous to formulate compositions of the present invention in dosage unit form for ease of administration and uniformity of dosage. Dosage unit form as used herein refers to physically discrete units suited for the patient. Each dosage unit contains a predetermined quantity of the virus comprising an alkyne-modified fatty acid moiety, an alkyne-modified carbohydrate moiety or an alkyne-modified isoprenoid lipid moiety calculated to produce a therapeutic effect in association with the carrier. The dosage unit depends on the characteristics of the virus comprising the alkyne-modified fatty acid moiety, the alkyne-modified carbohydrate moiety or the alkyne-modified isoprenoid lipid moiety and the particular therapeutic effect to be achieved.

Toxicity and therapeutic efficacy of the composition of the present invention can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used to formulate a dosage range in humans. The dosage of these compositions of the present invention may lie within the range of circulating concentrations of the virus comprising an alkyne-modified fatty acid moiety, an alkyne-modified carbohydrate moiety, or an alkyne-modified isoprenoid lipid moiety in the blood, that includes an $ED_{50}$ with little or no toxicity. The dosage may vary within this range depending upon the dosage composition form employed and the route of administration. For any composition comprising a virus comprising the alkyne-modified fatty acid moiety, the alkyne-modified carbohydrate moiety, or the alkyne-modified isoprenoid lipid moiety used in the methods described herein, the therapeutically effective dose can be estimated initially using cell culture assays. A dose may be formulated in animal models to achieve a circulating plasma concentration range that includes the $IC_{50}$ (i.e., the concentration of the such virus which achieves a half-maximal inhibition of symptoms). The effects of any particular dosage can be monitored by a suitable bioassay.

The compositions of present invention may also contain other active compounds providing supplemental, additional, or enhanced therapeutic functions. In one embodiment, the composition further comprises at least one anti-viral agent, such as a reverse transcriptase inhibitor, a virus protease inhibitor, a viral fusion inhibitor, a viral integrase inhibitor, a glycosidase inhibitor, an amphotericin B, hydroxyurea, α-interferon, β-interferon, γ-interferon, and an antisense oligonucleotide.

In one embodiment, the at least one reverse transcriptase inhibitor includes, but is not limited to, one or more nucleoside analogs, such as Zidovudine (AZT), Didanosine (ddI), Zalcitabine (ddC), Stavudine (d4T), Lamivudine (3TC), Abacavir (ABC), Emtricitabine (FTC), Entecavir (INN), Apricitabine (ATC), Atevirapine, ribavirin, acyclovir, famciclovir, valacyclovir, ganciclovir, and valganciclovir; one or more nucleotide analogs, such as Tenofovir (tenofovir disoproxil fumarate), Adefovir (bis-POM PMPA), PMPA, and cidofovir; or one or more non-nucleoside reverse transcriptase inhibitors, such as Efavirenz, Nevirapine, Delavirdine, and Etravirine.

In other embodiments, the at least one viral protease inhibitor includes, but is not limited to, tipranavir, darunavir, indinavir, lopinavir, fosamprenavir, atazanavir, saquinavir, ritonavir, indinavir, nelfinavir, and amprenavir.

In other embodiments, the at least one viral fusion inhibitor includes, but is not limited to a CD4 antagonist, such as soluble CD4 or an antibody that binds to CD4, such as TNX-355, BMS-806; a CCR5 antagonist, such as SCH-C, SCH-D, UK-427,857, maraviroc, vicriviroc, or an antibody that binds to CCR5, such as PRO-140; a CXCR4 antagonist, such as, AMD3100 or AMD070; or an antagonist of gp41, such as enfuvirtide.

In other embodiments, the at least one viral integrase inhibitor includes, but is not limited to, raltegravir.

In other embodiments, the at least one glycosidase inhibitor includes, but is not limited to, SC-48334 or MDL-28574.

The invention claimed is:

1. A human immunodeficiency virus comprising an alkyne-modified fatty acid moiety, wherein the moiety is non-naturally occurring, and wherein the alkyne-modified fatty acid moiety is 15-ethynylpentadecanyl or 12-ethynyldodecanyl.

2. The virus of claim 1, wherein the virus is HIV-1.

3. The virus of claim 1, wherein the virus is inactivated.

4. The virus of claim 1, wherein the virus is attenuated.

5. The virus of claim 1, wherein the alkyne-modified fatty acid moiety is 15-ethynylpentadecanyl.

6. The virus of claim 1, wherein the alkyne-modified fatty acid moiety is attached to the virus by an amide or a thioester bond.

7. A composition comprising the virus of claim 1.

8. The composition of claim 7, further comprising a pharmaceutically acceptable excipient.

9. The virus of claim 1, wherein the alkyne-modified fatty acid moiety is 12-ethynyldodecanyl.

10. An in vitro method of producing the human immunodeficiency virus of claim 1, the method comprising contacting the virus with the alkyne-modified fatty acid moiety in an amount effective to enhance the infectivity of the virus.

11. The method of claim 10, wherein the virus is in a cell.

12. The method of claim 11, wherein the cell is a human animal cell or a non-human animal cell.

13. The method of claim 10, wherein the human immunodeficiency virus is HIV-1.

14. The method of claim 10, wherein the contacting is performed in a solution comprising at least one of animal serum, amino acids, buffers, fatty acids, glucose, hormones, inorganic salts, lipids, metal ion chelators, peptides, surfactants, trace metals, and vitamins.

* * * * *